US008021868B2

(12) United States Patent
Su et al.

(10) Patent No.: US 8,021,868 B2
(45) Date of Patent: Sep. 20, 2011

(54) ANTI-ALLERGY LACTIC ACID BACTERIA

(75) Inventors: Wei-Chih Su, Shanhua Town (TW); Pei-Shan Hsieh, Shanhua Town (TW); Yi-Chun Tsai, Shanhua Town (TW); Chyi-Jang Wu, Shanhua Town (TW); Yi-Chun Chen, Shanhua Town (TW); Chung-Wei Kuo, Shanhua Town (TW); Chiung-Ying Yang, Shanhua Town (TW)

(73) Assignee: Promd Biotech Co., Ltd., Tainan County (TW)

( * ) Notice: Subject to any disclaimer, the term of this patent is extended or adjusted under 35 U.S.C. 154(b) by 930 days.

(21) Appl. No.: 11/937,429

(22) Filed: Nov. 8, 2007

(65) Prior Publication Data

US 2008/0166331 A1    Jul. 10, 2008

(30) Foreign Application Priority Data

Jan. 5, 2007 (TW) ................................ 96100486 A

(51) Int. Cl.
*C12N 1/20* (2006.01)

(52) U.S. Cl. ...................... 435/252.9; 435/853; 435/854

(58) Field of Classification Search .................... None
See application file for complete search history.

(56) References Cited

U.S. PATENT DOCUMENTS

| 6,379,663 | B1 | 4/2002 | Gill et al. |
| 6,994,848 | B2 | 2/2006 | Hsu et al. |
| 7,179,460 | B2 | 2/2007 | Dennin et al. |
| 7,183,108 | B1 | 2/2007 | Cayuela et al. |

FOREIGN PATENT DOCUMENTS

WO    WO-01/34186 A1    5/2001

OTHER PUBLICATIONS

Guidelines for the eva;uation of probiotics in food; Report of joint FAO/WHO working group on drafting guidelines for the evaluation of probitics in food; London Ontario, Canada, Apr. 30 and May 1, 2002 pp. 1-11.
Lilly et al., Probiotics: Growth-Promoting Factors Produced by Microorganisms, Science, New Series, vol. 147, No. 3659. (Feb. 12, 1965), pp. 747-748.
Schrezenmeir et al, "Probiotics, prebiotics, and synbiotics-approaching a definition[1-3]", Am J Clin Nutr 2001;73 pp. 361S-364S.
Macfarlane et al., "Chemotaxonomic Analysis of Bacterial Populations Colonizing the Rectal Mucosa in Patients with Ulcerative Colitis" Clenical Infectious Diseases, 38, Jun. 15, 2004 pp. 1690-1699.
Bjorksten et al., "The intestinal micoflora in allergic Estonian and Swedish 2-year-old children" Clenical and Experimental Allergy, vol. 29, (1999) pp. 342-346.
Cross et al., "Anti-alleregy properties of fermented foods: an important immunoregulatory mechanism of lactic acid bacteria?", International Immunopharmacology, 1, (2001) pp. 891-901.
Matsuzaki et al., "The effect of Oral Feeding of *Lactobacillus casei* Strain Shirota of Immunoglobulin E Production in Mice" , Journal Diary Science vol. 81, (1998), pp. 48-53.
Murosaki et al., "Heat-killed *Lactobacillus plantarum* L-137 suppresses naturally fed antigen-specific IgE production by stimulation of IL-12 production in mice.", Basic and clinical immunology vol. 102, (1998), pp. 57-64.
Shimada et al., "Effect of lysed *Enterococcus faecalis* FK-23 (LFK) on allergen-induced pertoneal accumulation of eosinophils in mice", Clin Exp Allergy (2003), vol. 33, pp. 684-687.
Kalliomamaki et al., "Probiotics in primary prevention of atopic disease: a randomised placebo-controlled trial", The Lancet, vol. 357, Apr. 7, 2001, pp. 1076-1079.
Kalliomaki et al., "Probiotics and prevention of atopic disease: 4-year follow-up of a randomised placebo-controlled trial." The Lancet, Col. 361, May 31, 2003, pp. 1869-1871.
Rosenfeldt et al., "Effect of probiotic *Lactobacillus* strains in children with atopic dermatitis", J Allergy Clin Immunol, (2003) vol. 111, pp. 389-395.
Kato et al.,"Latic acid bacterium potently induces the production of interleukin-12 and interferon-γ by mouse splenocytes" International Journal of Immonopharmacology vol. 21 (1999) pp. 121-131.
Fujiwara et al., "The Anti-Allergoc Effects of Lactic Acid Bacteria Are Strain Dependent and Mediated by Effects on both Th1/Th2 Cytokine Expression and Balance", International Articles of Allergy and Immunology, (2004), vol. 135 pp. 205-215.
Lin et al., "Polysaccharide purified from *Ganoderma lucidum* induced activation and maturation of human monocyte-derived dendritic cells by the NF-κB and p38 mitogen-activated protein kinase pathways" Journal of Leukocyte Biology vol. 78, Aug. 2005, pp. 533-543.
Charng et al., "Inhibition of allergen-induced airway inflammation and hyperreactivity by recombinant lactic-acid bacteria", Vaccine vol. 24 (2006), pp. 5931-5936.

*Primary Examiner* — Debbie K Ware
(74) *Attorney, Agent, or Firm* — Rosenberg, Klein & Lee

(57) ABSTRACT

The invention described relates to novel strains of lactic acid bacteria and their use in anti-allergy. The composition may be in the form of foodstuffs or in the form of pharmaceutical compositions.

1 Claim, 11 Drawing Sheets

ANTI-ALLERGY LACTIC ACID BACTERIA

BACKGROUND OF THE INVENTION

1. Field of the Invention

The invention relates to novel strains of lactic acid bacteria. The composition comprising of *Lactobacillus acidophilus* PM-A0002, *Lactobacillus gasseri* PM-A0005, *Lactobacillus salivarius* PM-A0006, *Lactobacillus johnsonii* PM-A0009 and *Lactobacillus acidophilus* PM-A0013 and their use for treating allergy related diseases.

2. Background

The recent increase in allergic diseases such as atopic dermatitis, atopic eczema, and allergic rhinitis has been, and continues to be, a serious social problem in many countries. There is a theory which implies that allergy and asthma have increased during the last 20 to 50 years because of a reduced exposure in childhood to bacterial and viral infections brought about by improvements in public health measures such as vaccination and sanitation. Allergic diseases are reported to be caused by a skew in the balance between T helper type 1 (Th1) and 2 (Th2) cells. Classical allergy is a type 2 hypersensitivity reaction mediated by the interaction of mast cells and eosinophils coated with allergen-specific IgE and a cross-lining allergen. Few lactic acid bacteria have been shown to stimulate Th1 related cytokines secretion, they have the potential to either prevent or ameliorate disease conditions or both.

The term probiotic is derived from the Greek and literally translates as 'for-life'. It was first used by Lilly et al in 1965 (Lilly D M and Stillwell R H, 1965, Science, 14: 747-748). Probiotics are live microbial food supplements that can change either the composition and/or the metabolic activities of the microbiota or modulate immune system reactivity in a way that benefits health. Rarker described probiotics as "organisms and their secreted substances which contribute to an intestinal microbial balance." A recent detailed definition of probiotics is "a preparation of or a product containing viable, defined microorganisms in sufficient numbers to alter the existing microflora (by displacement or colonization) in the intestine of the host and thereby exert beneficial health effects (Schrezenmeir J, de Vrese M, 2001, Am J Clin Nutr, 73: 361S-364S). Probiotics are now commonly available over the counter and in the chiller cabinet of every supermarket as bio-yoghurts, probiotic drinks or food supplements. Few different microorganisms have been used as probiotics, the most common being the lactic acid bacteria. Lactic acid bacteria are members of the commensal microflora of a healthy human colon. They can be found on food particles in the lumen of the gut and in the mucus overlying the epithelial cell barrier, putting them in very close proximity to the human host (Macfarlanc S, Furrie E, Cummings J H and Macfarlanc G T, 2004, Clinical Infectious Diseases, 38: 1690-1699). The possible function of probiotics are varied and include the production and secretion of antimicrobial substances, a stimulus to the host's immune responses, and displacement of pathogen colonization. They provide health benefits to the host by stimulating metabolic activities or by protecting against conditions such as intestinal infection, food allergies, and colon cancer.

Otherwise, the current state of evidence suggests that probiotic effects are strain specific. Strain identity is important to link a strain to a specific health effect as well as to enable accurate surveillance and epidemiological studies. So we must use in vitro tests that to screen potential probiotic strains. In vitro tests are useful to gain knowledge of strains and the mechanism of the probiotic effect. However, it was noted that the currently available tests are not fully adequate to predict the functionality of probiotic microorganisms in the human body. It was also noted that in vitro data available for particular strains are not sufficient for describing them as probiotic. Probiotics for human use will require substantiation of efficacy with human trials. Appropriate target-specific in vitro tests that correlate with in vivo results are recommended. For example, in vitro bile salts resistance was shown to correlate with gastric survival in vivo. The seven points of the main currently used in vitro tests for the study of probiotic strains are first is resistance to gastric acidity, second is bile acid resistance, third is adherence to mucus and/or human epithelial cells and cell lines, forth is antimicrobial activity against potentially pathogenic bacteria, fifth is ability to reduce pathogen adhesion to surfaces, sixth is bile salt hydrolase activity, seventh is resistance to spermicides (Guidelines for the evaluation of probiotics in food; Report of joint FAO/WHO working group on drafting guidelines for the evaluation of probiotics in food; London Ontario, Canada April 30 and May 1, 2002).

Allergic children in Estonia and Sweden were found to be less often colonized with lactobacilli compared with nonallergic children (Björksten B, Naaber P, Sepp E and Mikelsaar M, 1999, Clinical and Experimental Allergy, 29: 342-346).

Lactobacilli are thought to induce Th1 reaction and improve allergic diseases (Cross M L, Stevenson L M and Gill H S, 2001, International Immunopharmacology, 1: 891-901).

Furthermore, orally administered heat-treated *Lactobacillus casei* (strain Shirota) was found to inhibit IgE production induced by ovalbumin in mice serum (Matsuzaki T, Yamazaki R, Hashimoto S and Yokokura T, 1998, Journal Dairy Science, 81: 48-53).

Moreover, intraperitoneally injected heat-treated *Lactobacillus plantarum* L-137 was demonstrated to suppress IgE production in response to a casein allergy in mice (Murosaki S, Yamamoto Y, Ito K, Inokuchi T, Kusaka H, Ikeda H and Yoshikai Y, 1998, J. Allergy Clin. Immunol, 102: 57-64).

Oral administration of lysed *Enterococcus faecalis* FK-23 resulted in a decrease of peritoneal accumulation of eosinophils induced by ragweed pollen (Shimada T, Cheng L, Ide M, Fukuda S, Enomoto T, Shirakawa T, 2003, Clin Exp Allergy, 33: 684-687).

In humans, *Lactobacillus rhamnosus* strain GG administered in the perinatal period reduced the incidence of atopic eczema in children at risk during the first 2 years of life (Kalliomäki M, Salminen S, Arvilommi H, Kero P, Koskinen P and Isolauri E, 2001, Lancet 357: 1076-1079) and beyond infancy (Kalliomäki M, Salminen S, Poussa T, Aivilommi H and Isolauri E, 2003, Lancet 361: 1869-1871).

*Lactobacillus rhamnosus* 19070-2 and *Lactobacillus reuteri* DSM 122460 improved moderately the clinical severity of eczema in children with atopic dermatitis (Rosenfeldt V; Benfeldt E, Nielsen S D, Michaelsen K F, Jeppesen D L, Valerius N H and. Paerregaard A, 2003, J. Allergy Clin. Immunol. 111:389-395).

SUMMARY OF THE INVENTION

The invention related to novel lactic acid bacterial strains comprising of *Lactobacillus acidophilus* PM-A0002, *Lactobacillus gasseri* PM-A0005, *Lactobacillus salivarius* PM-A0006, *Lactobacillus johnsonii* PM-A0009, *Lactobacillus acidophilus* PM-A0013.

In another aspect, the invention may be said broadly to consist of a composition of a biologically pure culture of any one of *Lactobacillus acidophilus* PM-A0002, China Center for Type Culture Collection (CCTCC) deposit number M 207038 dated Apr. 6, 2007, *Lactobacillus gasseri* PM-A0005, CCTCC deposit number M 207039 dated Apr. 6, 2007, *Lactobacillus salivarius* PM-A0006, CCTCC deposit number M 207040 dated Apr. 6, 2007, *Lactobacillus johnsonii* PM-A0009, CCTCC deposit number M 207041 dated Apr. 6, 2007, *Lactobacillus acidophilus* PM-A0013, CCTCC deposit number M 207042 dated Apr. 6, 2007 in an anti-allergy stimulating concentration, with a physiologically acceptable excipient or diluent.

In one embodiment said composition contains any one or more of said strains.

Preferably said physiologically acceptable excipient or diluent is a food.

Preferably said food is any one of cultured milk, yoghurt, cheese, milk drink, milk powder, coffee or tea.

Alternatively said composition is a pharmaceutical composition and said excipient or diluent is pharmacologically acceptable excipient or diluent.

In another aspect, the invention may be said broadly to consist of a method of enhancing IL12 or IFN-gamma which are Th1 cytokines and modifying conditions of allergy which comprise administering to a mammal any one of the above biologically pure cultures at an anti-allergy stimulating dosage rate.

In one embodiment said composition contains any one or more of said strains.

Preferably said physiologically acceptable excipient or diluent is a food.

Preferably said food is any one of cultured milk, yoghurt, cheese, milk drink, milk powder, coffee or tea.

Alternatively said composition is a pharmaceutical composition and said excipient or diluent is pharmacolohically acceptable excipient or diluent.

Anti-allergy, physiologically acceptable, biologically pure strains of homologues or mutants of any one of the strains:
  *Lactobacillus acidophilus* PM-A0002
  *Lactobacillus gasseri* PM-A0005
  *Lactobacillus salivarius* PM-A0006
  *Lactobacillus johnsonii* PM-A0009
  *Lactobacillus acidophilus* PM-A0013

In another embodiment the invention may be said broadly to consist of a method of anti-allergy which comprises administering to a mammal any one of the above biologically pure cultures at an immunostimulating dosage rate.

In another embodiment substantially biologically pure cultures of one or more of the above-defined strains are present.

Preferably said culture is administered in the form of a composition with a physiologically acceptable excipient or diluent.

Preferably said physiologically acceptable excipient or diluent is a food.

Preferably said food is cultured milk, yoghurt, cheese, milk drink or milk powder.

This invention may also be said broadly to consist in the parts, elements and features referred to or indicated in the specification of the application, individually or collectively, and any or all combinations of any one or more of said parts, elements or features, and where specific integers are mentioned herein which have known equivalents in the art to which this invention relates, such known equivalents are deemed to be incorporated herein as if individually set forth.

Figure 7:
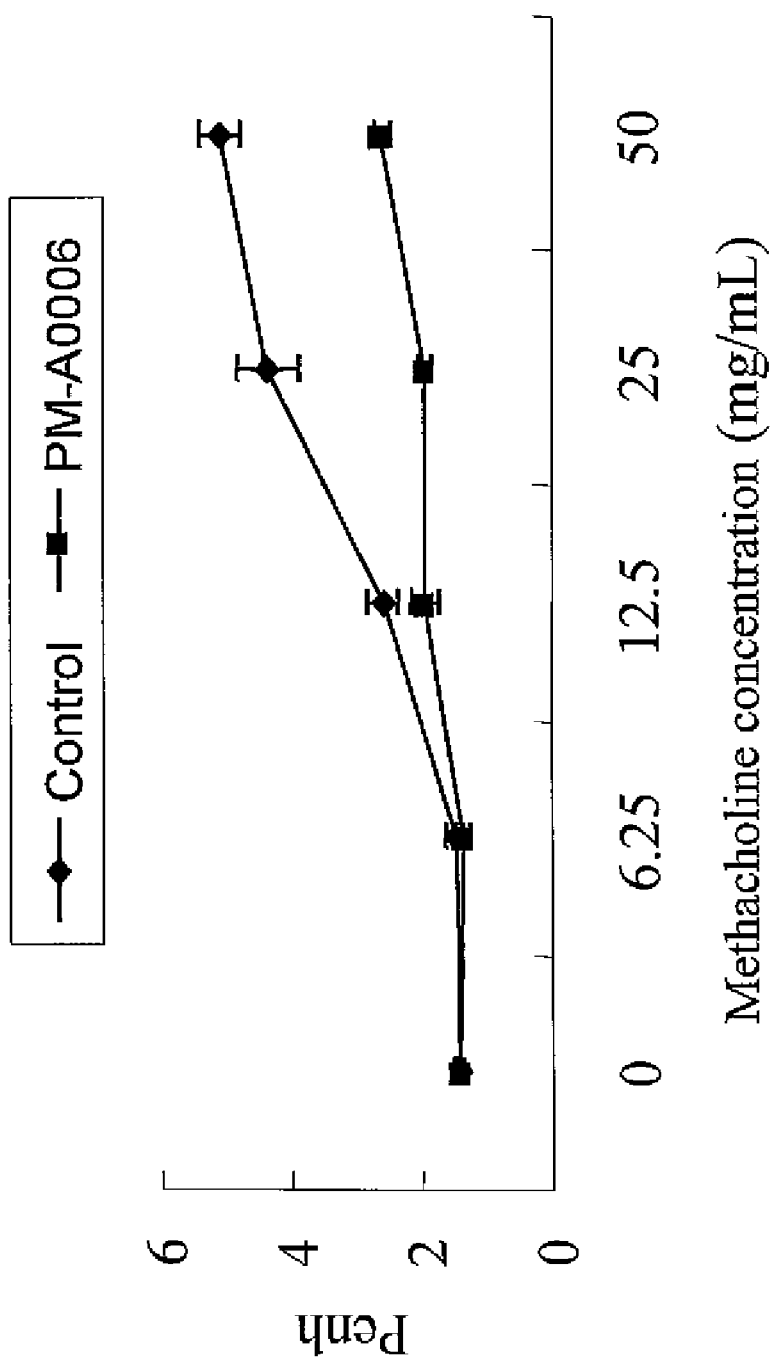

FIG. 7 shows the readings for breathing parameters for a period of 3 min subsequent to each nebulization with AHR values were determined. The *Lactobacillus salivarius* PM-A0006 can suppress allergen-induced AHR which compared with control group (P<0.05). Airway responsiveness to aerosolized methacholine was measured in unrestrained, conscious mice. Basal values were measured, followed by measuring the response to nebulized saline and increasing concentrations of methacholine (0, 6.25, 12.5, 25 and 50 mg/mL). Readings for breathing parameters for a period of 3 min subsequent to each nebulization with Penh were determined.

Figure 8:
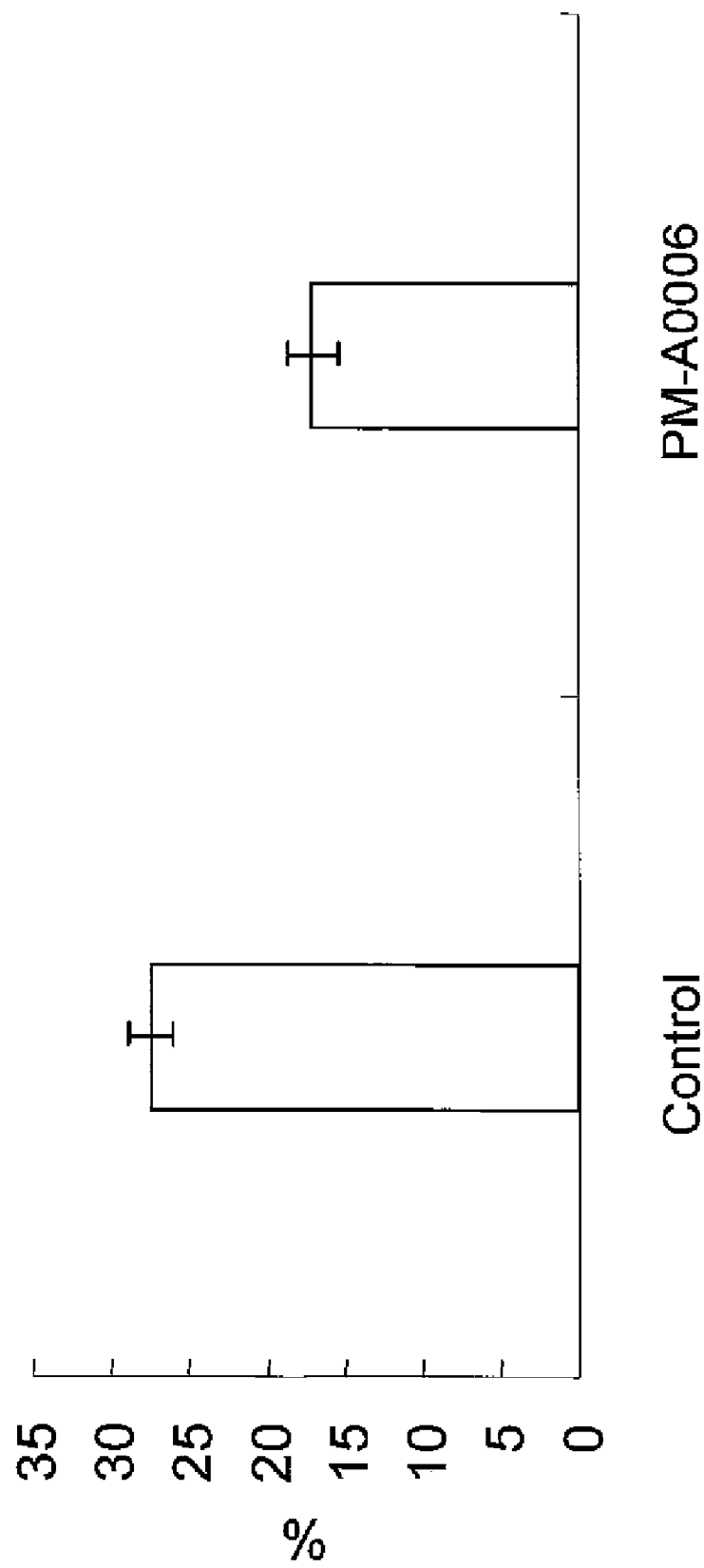

FIG. 8 shows the number of eosinophils in the brochoalveolar lavage of ovalbumin-sensitized mice treated with PM-A0006. The number of cells in the BALF was used as a measure of the relative infiltration of cells into the airways. Significantly low numbers of eosinophils in the BALF of PM-A0006-treated mice were observed, when compared to control groups.

Figure 9:
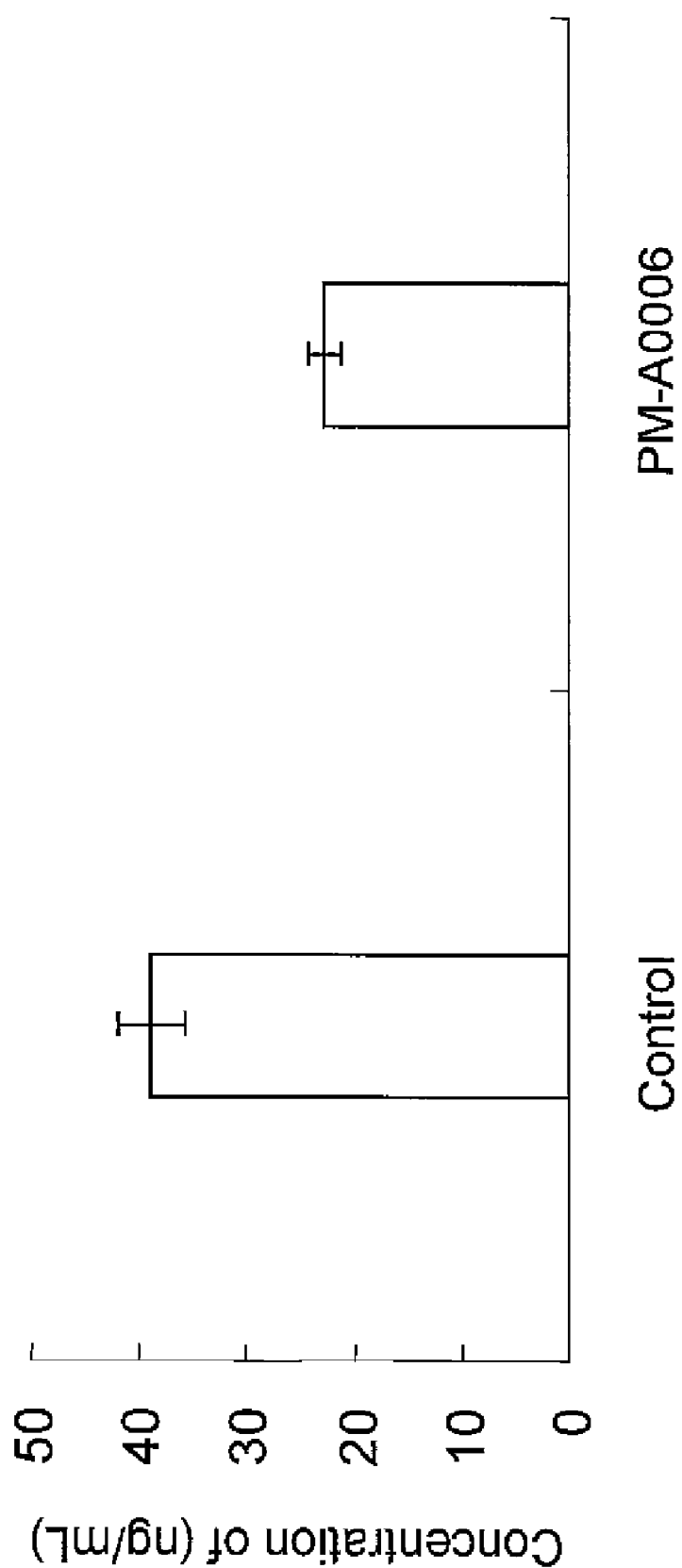

FIG. 9 shows concentration of eotaxin in the brochoalveolar lavage of ovalbumin-sensitized mice treated with PM-A0006. The chemokine of supernatant in the BALF were detected by ELISA. Significantly low concentrations of eotaxin in the BALF of PM-A0006-treated mice were observed, when compared to control groups.

Figure 10:
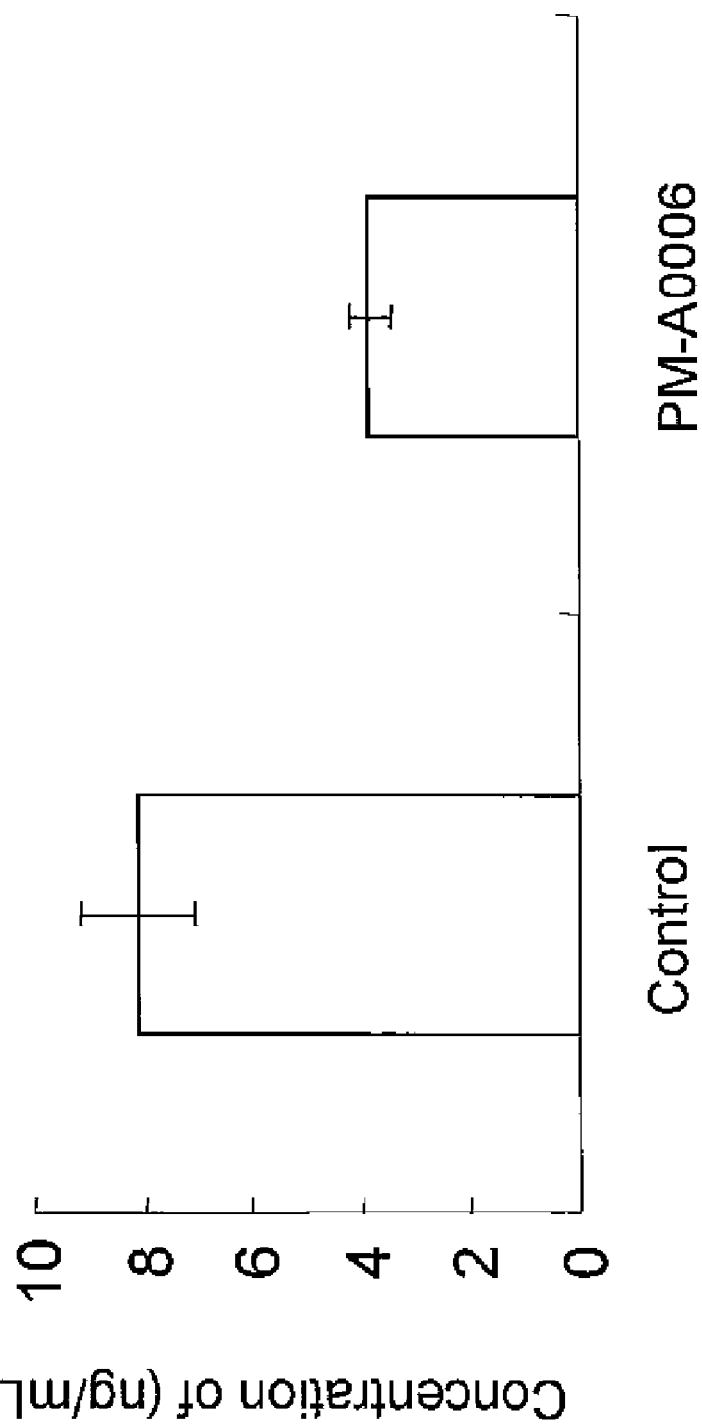

FIG. 10 shows concentration of $PGE_2$ in the brochoalveolar lavage of ovalbumin-sensitized mice treated with PM-A0006. The cytokine of supernatant in the BALF were detected by ELISA. Lower concentrations of $PGE_2$ in the BALF of PM-A0006-treated mice were observed, when compared to control groups.

Figure 11:
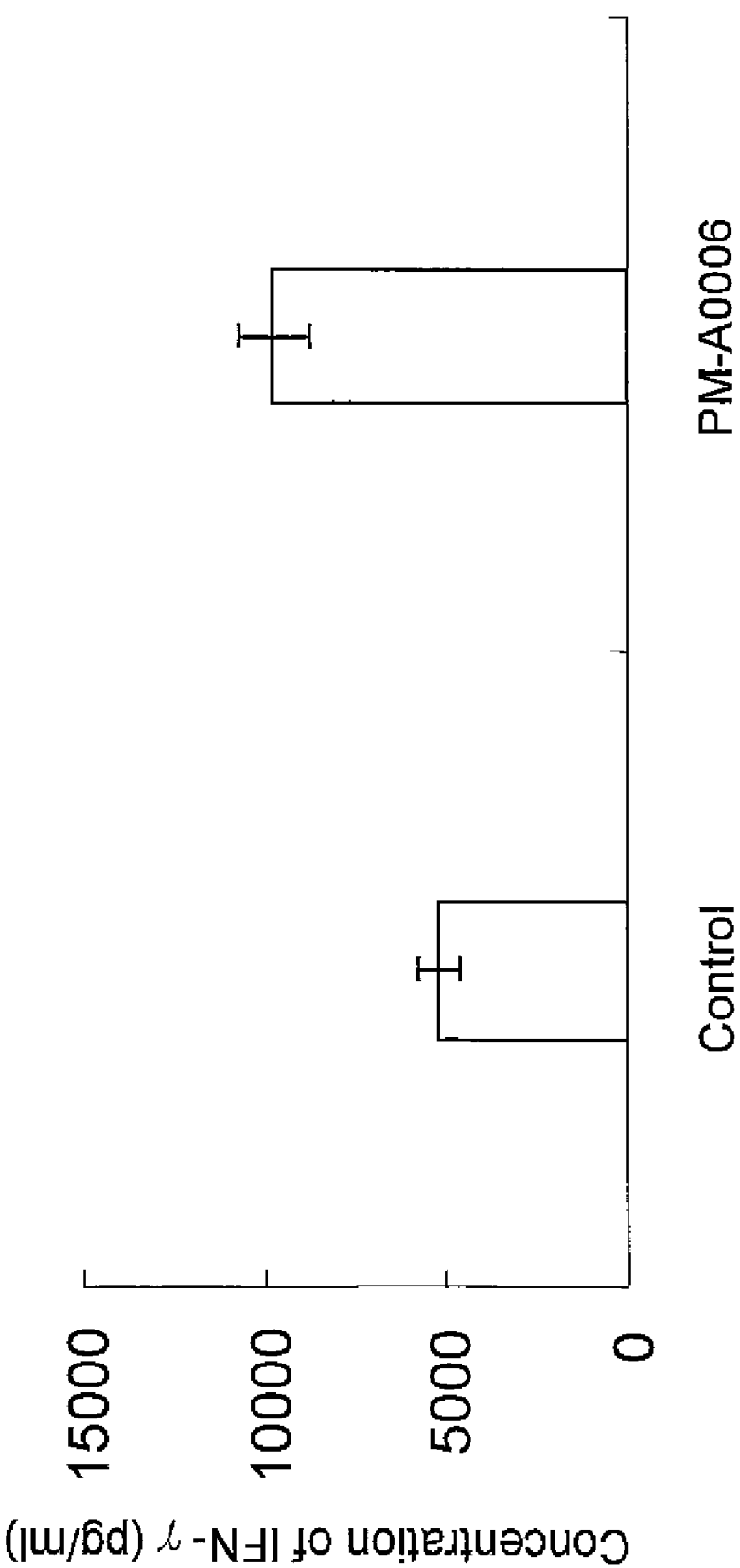

FIG. 11 shows the secretion of IFN-gamma from splenocytes which were control mice (placebo group) or PM-A0006-treated mice in culture following the addition of ConA was determined. ConA induced IFN-gamma production by splenocytes the co-culture of a *Lactobacillus* strain and peripheral blood mononuclear cells (PBMC). The secretions of IFN-gamma were detected with ELISA after 48-hour co-culture of the lactic acid bacterium and PBMCs, respectively. The amounts of IFN-.gamma were expressed by the absorbance values (O.D. values) shows the secretion of IFN-gamma from splenocytes which were control mice (placebo group) or PM-A0006-treated mice in culture following the addition of ConA was determined. ConA induced IFN-gamma production by splenocytes which was *Lactobacillus salivarius* PM-A0006-treated mice group higher than control mice group. ConA induced IFN-gamma production by splenocytes which were control mice or PM-A0006-treated mice were cultured with constant concentration (5 μg/mL) of ConA. After 48 h cultivation, the culture supernatant was collected. The IFN-gamma levels were determined by ELISA.

DETAILED DESCRIPTION OF THE INVENTION

The invention may be said broadly to consist of a composition of a biologically pure culture of any one of *Lactobacillus acidophilus* PM-A0002, CCTCC deposit number M 207038 dated Apr. 6, 2007, *Lactobacillus gasseri* PM-A0005, CCTCC deposit number M 207039 dated Apr. 6, 2007, *Lactobacillus salivarius* PM-A0006, CCTCC deposit number M 207040 dated Apr. 6, 2007, *Lactobacillus johnsonii* PM-A0009, CCTCC deposit number M 207041 dated Apr. 6, 2007, *Lactobacillus acidophilus* PM-A0013, CCTCC deposit number M 207042 dated Apr. 6, 2007.

The invention comprising of five latic acid bacterial strains are deposited at China Center for Type Culture Collection. This deposited center address is Wuhan University, Wuhan, China. Zip Code is 430072. Table 1 shows the detailed deposited data.

TABLE 1

Deposited data of the lactic acid bacteria.

| Name of *Lactobacilli* | Deposited number | Deposited date |
|---|---|---|
| *Lactobacillus acidophilus* PM-A0002 | M 207038 | Apr. 6, 2007 |
| *Lactobacillus gasseri* PM-A0005 | M 207039 | Apr. 6, 2007 |
| *Lactobacillus salivarius* PM-A0006 | M 207040 | Apr. 6, 2007 |
| *Lactobacillus johnsonii* PM-A0009 | M 207041 | Apr. 6, 2007 |
| *Lactobacillus acidophilus* PM-A0013 | M 207042 | Apr. 6, 2007 |

These five Lactobacilli were discovered special function which is decrease and modify condition of allergy. The allergy conditions which contain airway hyperreactivity and inflammation, atopic dermatitis, allergic conjunctivitis, rhinitis, sinusitis, hypersensitive pneumonia, extrinsic allergic alveolitis, urticaria, eczema, anaphylaxis, angioedema, allergic and migraine headache, certain gastrointestinal disorders, and asthma.

Materials and Methods

In Vitro Test
Preparation of Human Peripheral Blood Mononuclear Cells (PBMC) and Determination of Cytokines.

PBMC were obtained from healthy donors by centrifugation with Ficoll-Hypaque, and the light-density fraction from the 42.5-50% interface was recovered. Cytokines including and IFN-gamma in the culture supernatants from PBMC and lactobacillus cells were cultured together. PBMC ($1 \times 10^6$ cells/well) and lactobacillus cells were incubated at a ratio of 1:10 at 37° C. for 48 h. The culture supernatant was obtained from 48 h cultures. The content of IFN-gamma in the culture supernatants was assayed by the sandwich ELISA method.
Preparation of Human Dendritic Cells and Determination of Cytokines Human dendritic cells were generated from PBMC. $CD14^+$ cells were purified by positive selection using anti-$CD14^+$ microbeads in conjunction with the MiniMACS system by following the manufacturer's instructions (Miltenyi Biotec., Auburn, CA). The $CD14^+$ cells were cultured at $1 \times 10^6$ cells per 1 mL of RPMI-1640 containing 10% fetal bovine serum in 24-well plates with human granulocyte macrophage-colony stimulating factor (hGM-CSF; 800 U/mL) and human IL-4 (500 U/mL). Fresh medium containing hGM-CSF and IL-4 was added every 2-3 days. Human monocyte-derived dendritic cells were used routinely at day 6 of culture. Cytokines including IL-12 in the culture supernatants from dendritic cells and lactobacillus cells were cultured together. Dendritic cells ($1 \times 10^6$ cells/well) and lactobacillus cells were incubated at a ratio of 1:10 at 37° C. for 48 h. The culture supernatants were obtained from 48 h cultures. The content of IL-12 in the culture supernatants was assayed by the sandwich ELISA method.
Acid and Bile Tolerance Acid and bile tolerance of the lactic acid bacteria were studied by incubating in MRS broth supplemented with pH 2.5 and 1.5% oxgall. The pH was adjusted to 2.5 with hydrochloric acid and lactic acid bacteria were incubated at 37° C.

for 3 h. The 1.5% oxgall cultures were incubated at 37° C. for 4 h. Each of these five lactobacilli were subcultured at least three times before experimental use, followed by centrifugation after the final subculture, inoculation into the broth, and growth monitoring using the plate count method. Acid and bile tolerance were determined by comparing the final plate count after 24 h.

Adhesion to Intestinal Cells

Caco-2 cells in a monolayer were washed twice with PBS, 1.5 mL of MEM was added to each dish, and the dishes were incubated for 1 h before inoculation of lactic acid bacteria. Overnight cultures of lactic acid bacteria were appropriately diluted with MEM to give a lactobacillus cells concentration of approximately $10^8$ cfu/mL, and 1.5 mL was used to inoculate the Caco-2 cells. After incubation for 1 h at 37° C., all of the dishes were washed four times with PBS to release unbound lactic acid bacteria. The lactic acid bacteria were then fixed with 3 mL of methanol and incubated for 5 to 10 min at room temperature. After removal of the methanol, the cells were stained with Gram's stain. Each adhesion assay was performed in triplicate with cells from three successive passages (8 to 13 cell passages).

In Vivo Test

Animals Model for Asthma and Study Protocol

Figure 5:
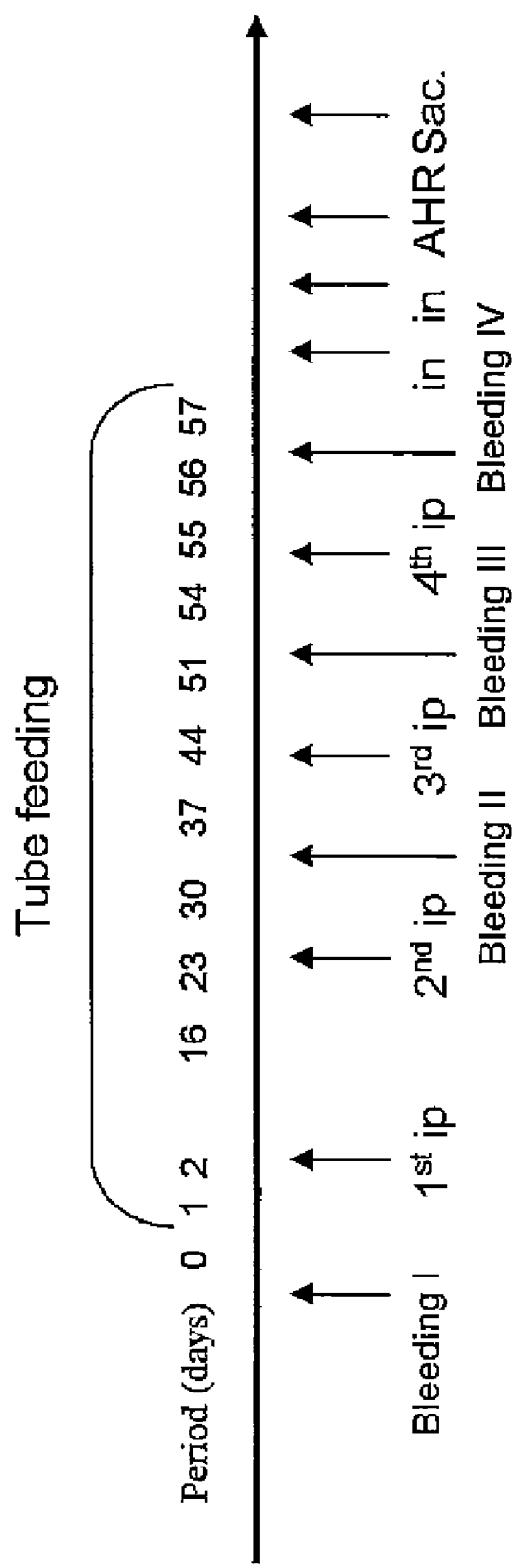
FIG. 5 shows the process of asthma animal model. Animals were actively sensitized by intra-peritoneal injection of 50 μg ovalbumin emulsified in 4 mg aluminum hydroxide in the total volume of 100 μL on Days 2, 16, 30 and 44. After actively sensitized, animals were induced airway responsiveness by intra-nasal dripping of 100 μg/10 μL ovalbumin on Days 54 and 55. Mice received lactobacillus cells $2.6 \times 10^6 \sim 2.6 \times 10^7$ CFU everyday for eight weeks.

Female BALB/c mice, aged between six and eight weeks, were obtained from the College of Medicine Laboratory Animal Center, National Taiwan University (they originating from the Jackson Laboratory, Bar Harbor, Me., USA), and were divided into different groups for each experiment. There were 14 test mice in each group. Animals were actively sensitized by intra-peritoneal injection of 50 μg ovalbumin emulsified in 4 mg aluminum hydroxide in the total volume of 100 μL on Days 2, 16, 30 and 44. After actively sensitized, animals were induced airway responsiveness by intra-nasal dripping of 100 μg/10 μL ovalbumin on Days 54 and 55. The process was shown in FIG. 5. Mice oral uptakes target lactobacillus $2.6 \times 10^6 \sim 2.6 \times 10^7$ CFU/day for eight weeks. Twenty-four hours after such inhalational challenge, pulmonary airway resistance was measured, and bronchoalveolar lavage fluid (BALF) and serum and splenocyte were collected.

Determination of Ovalbumin-Specific IgE

The level of ovalbumin-specific IgE was determined by ELISA. Protein high-binding plates were coated with 100 μL of 0.5 mg ovalbumin diluted in coating buffer (0.1 M $NaHCO_3$, pH=8.2). Following overnight incubation at 4° C., plates were washed three times and blocked with 1% (wt/vol) BSA-PBS buffer for 2 h at 25° C., plates were washed three times. Sera were used for ovalbumin-specific IgE measurement. Following overnight incubation at 4° C., plates were washed four times. Biotin-conjugated monoclonal rat anti-mouse IgE was used at a 1:100 dilution and was added for incubation for 1-2 h at 25° C., plates were washed five times. Avidin-horseradish peroxidase conjugated (1:1000) was then added and incubation continued for 1 h at 25° C., plates were washed six times. The color reaction was developed with the addition of ABTS (2,2'-Azino-bis-3-Ethylbenzthiazoline-6-Sulfonic Acid) for 30 minutes at 25° C. To add 5% SDS for stopped reaction. Plates were read in a microplate autoreader at a wavelength of 450 nm. The results were expressed by ELISA unit. ELISA unit were calculated by the following equations:

$$\text{ELISA unit} = (Abs._{sample} - Abs._{blank})/(Abs._{positive\ control} - Abs._{blank})$$

Determination of Airway Responsiveness

Using barometric whole-body plethysmography (WBP; Biosystem X A, Buxco Electronics Inc. Sharon, Conn., USA), the response to inhaled methacholine for conscious. Mice were obtained and averaged for 3 min. Aerosized saline, followed by increasing concentrations of methacholine (ranging from 0, 6.25, 12.5, 25 and 50 mg/mL), was nebulized for 3 min, following which reading were taken and averaged for 3 min, this occurring subsequent to each nebulization event. Airway responsiveness was expressed as the Penh value per dose of methacholine.

Assessment of Cells and Supernatant in Bronchoalveolar Lavage Fluids (BALF)

Following the measurement of lung-function parameters, mice were cannulated and lavaged with 1 mL aliquots of 2% BSA in HBSS (Hank's balanced salt solution) buffer through a polyethylene tube introduced through the tracheostomy. Lavage fluid was collected and then centrifuged (500×g for 10 min at 4° C.), and the cell pellet so obtained was resuspended in 1 mL of 2% BSA in HBSS buffer. Cells supernatant was collected and determined eotaxin and $PGE_2$ by ELISA. Total cell counts were conducted by adding 10 μL of the cell suspension to 90 μL of 0.4% trypan blue following which the cells were counted under a light microscope in a chamber. Differentiated cell counts were made from cytospin preparations stained by Liu's stain. Cells were identified and differentiated into the following groups: eosinophils, lymphocytes, neutrophils, and macrophages by standard morphological techniques, for which 500 cells needed to be counted under 1000-fold magnification and the percentage and absolute number of each cell type was estimated.

Preparation of Spleen Cells Suspension and Determination of Cytokines

Mice were sacrificed by cervical dislocation following deep anesthesia. Their spleens were aseptically removed. Single-cell suspensions were then prepared by gently tearing each spleen against sterile glass slide and removing the red blood cells using Tris-buffered $NH_4Cl$ solution. The cells were washed three times in cold HBSS (Hank's balanced salt solution) buffer and then resuspended in RPMI-1640 medium supplemented with 5% fetal bovine serum (FBS), 1% penicillin-streptomycin mixture, and 5 μg/mL ConA. Splenocytes ($5 \times 10^6$ cells/well) were incubated at 37° C. for 48 h. The culture supernatant was obtained from 48 h culture. The content of IFN-gamma in the culture supernatants was assayed by the sandwich ELISA method. Briefly, microtiter plates were coated with 1 μg/mL of anti-IFN-gamma in 50 mM carbonate buffer (pH 9.6) overnight at 4° C., and then the wells were washed three times. After blocking with 1% (wt/vol) BSA-PBS buffer for 1 h at 25° C., samples were added to each well and the plates were incubated for 2 h at 37° C. The wells were then washed four times. Bound IFN-gamma was detected by biotin-conjugated anti-IFN-gamma antibody and streptoavidine-conjugated peroxidase. After the wells were washed five times, TMB (Tetramethylbenzidine) substrate was added to each well. The optical density (OD) was measured at 450 nm.

Statistical Analysis

The data were present by Means ±SDs (in vitro data) or Means ±SEMs (in vivo data). The significance of differences in the data was estimated using Student's t-test, with the significance level set at $P<0.05$, with difference level set at $P<0.1$.

EXAMPLE

Example 1

Morphology and General Property

These five lactobacilli species were confirmed its character by 16S rDNA sequence and API identification system result in taxonomy. The PM-A0002 which is ProMD Biotech Co., Ltd. number was identified as *Lactobacillus acidophilus*. The PM-A0005 which is ProMD Biotech Co., Ltd. number was identified as *Lactobacillus gasseri*. The PM-A0006 which is ProMD Biotech Co., Ltd. number was identified as *Lactobacillus salivarius*. The PM-A0009 which is ProMD Biotech Co., Ltd. number was identified as *Lactobacillus johnsonii*. The PM-A0013 which is ProMD Biotech Co., Ltd. number was identified as *Lactobacillus johnsonii*. Table 2 shows these five lactobacilli detailed structure and general property data.

TABLE 2

Morphology and general property of *lactobacilli*

*Lactobacillus acidophilus* PM-A0002:

The microorganism presents a short bar form or slightly long, the both ends is a circular, usually appear alone, become pair to or become short chain form, which grow on MRS broth.
The microorganism belongs to the group of lactic bacteria: Gram positive, catalase negative, non-sporeforming, anaerobic (facultative or occasionally obligate) rods, doesn't produce air when the glucose metabolizes, which grow on MRS agar, incubate anaerobically for 24 hours at 37° C. ± 1° C.

*Lactobacillus gasseri* PM-A0005:

The microorganism presents a short bar form or slightly long, the both ends is a circular, usually appear alone, become pair to or become short chain form, which grow on MRS broth.
The microorganism belongs to the group of lactic bacteria: Gram positive, catalase negative, non-sporeforming, anaerobic (facultative or occasionally obligate) rods, doesn't produce air when the glucose metabolizes, which grow on MRS agar, incubate anaerobically for 24 hours at 37° C. ± 1° C.

*Lactobacillus salivarius* PM-A0006:

The microorganism presents a short bar form, the both ends is a circular, usually appear alone, become pair to or become short chain form, which grow on MRS broth.
The microorganism belongs to the group of lactic bacteria: Gram positive, catalase negative, non-sporeforming, anaerobic (facultative or occasionally obligate) rods, doesn't produce air when the glucose metabolizes, which grow on MRS agar, incubate anaerobically for 24 hours at 37° C. ± 1° C.

*Lactobacillus johnsonii* PM-A0009:

The microorganism presents a short bar form or slightly long, the both ends is a circular, usually appear short chain form, which grow on MRS broth.
The microorganism belongs to the group of lactic bacteria: Gram positive, catalase negative, non-sporeforming, anaerobic (facultative or occasionally obligate) rods, doesn't produce air when the glucose metabolizes, which grow on MRS agar, incubate anaerobically for 24 hours at 37° C. ± 1° C.

*Lactobacillus acidophilus* PM-A0013:

The microorganism presents a short bar form or slightly long, the both ends is a square, usually appear chain form, which grow on MRS broth.
The microorganism belongs to the group of lactic bacteria: Gram positive, catalase negative, non-sporeforming, anaerobic (facultative or occasionally obligate) rods, doesn't produce air when the glucose metabolizes, which grow on MRS agar, incubate anaerobically for 24 hours at 37° C. ± 1° C.

Example 2

Human PBMC and Different *Lactobacillus* Strains were Co-Cultured and Harvested Culture Supernatant. Determination of IFN-Gamma in the Supernatant Detection these five lactobacilli: *Lactobacillus acidophilus* PM-A0002, *Lactobacillus gasseri* PM-A0005, *Lactobacillus salivarius* PM-A0006, *Lactobacillus johnsonii* PM-A0009, *Lactobacillus acidophilus* PM-A0013 which cocultured with PBMC can increase Th1 pathway cytokine, such as IFN-gamma. This method can screen anti-allergy lactobacilli.

Figure 1:
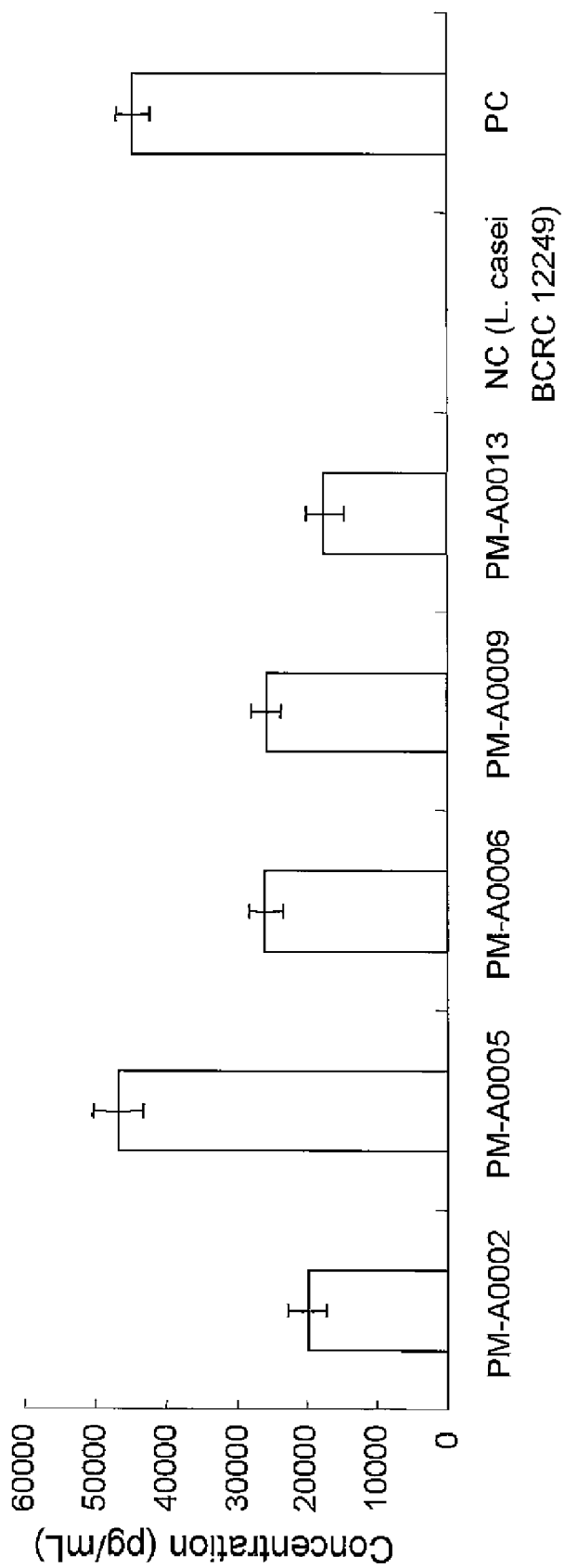
FIG. 1 shows the secretion of IFN-gamma in the co-culture of a *Lactobacillus* strain and peripheral blood mononuclear cells (PBMC). The secretions of IFN-gamma were detected with ELISA after 48-hour co-culture of the lactic acid bacterium and PBMCs, respectively. The amounts of IFN-gamma were expressed by the absorbance values (O.D. values). In the test, phytohemagglutinin (PHA) was used as positive control; *Lactobacillus casei* BCRC 12249 was used as negative control; bar 1 represents *Lactobacillus acidophilus* PM-A0002; bar 2 represents *Lactobacillus gasseri* PM-A0005; bar 3 represents *Lactobacillus salivarius* PM-A0006; bar 4 represents *Lactobacillus johnsonii* PM-A0009; bar 5 represents *Lactobacillus acidophilus* PM-A0013; bar 6 represents negative control; and bar 7 represents positive control.

The result is shown in table 3 and FIG. 1. The $10^5$~$10^7$ cells human PBMC were cultured with the $10^6$~$10^8$ cfu lactobacilli: *Lactobacillus acidophilus* PM-A0002, *Lactobacillus gasseri* PM-A0005, *Lactobacillus salivarius* PM-A0006, *Lactobacillus johnsonii* PM-A0009, *Lactobacillus acidophilus* PM-A0013, and the contents of IFN-gamma in the culture supernatant were determined by ELISA. IFN-gamma was detected after 48 hours cocultured. The negative control is *Lactobacillus casei* BCRC 12249 which is no anti-allergy effect. The positive control is phytohemagglutinin (PHA). The result showed that human PBMC can increase IFN-gamma secretion by these different *Lactobacillus* strains stimulating. There was significance of differences in the data.

TABLE 3

The secretion of IFN-gamma in the co-culture of a *Lactobacillus* strain and PBMC (Mean ± SD).

| Different *Lactobacillus* strain | IFN-gamma (pg/mL) |
| --- | --- |
| *Lactobacillus acidophilus* PM-A0002 | 19833 ± 2767 |
| *Lactobacillus gasseri* PM-A0005 | 46625 ± 3624 |
| *Lactobacillus salivarius* PM-A0006 | 25850 ± 2347 |
| *Lactobacillus johnsonii* PM-A0009 | 25725 ± 2008 |
| *Lactobacillus acidophilus* PM-A0013 | 17416 ± 2803 |
| Negative control (*L. casei* BCRC 12249) | 11 ± 2.3 |
| Positive control | 44666 ± 2488 |

Example 3

Human Dendritic Cells and *Lactobacillus* Cells were Co-Cultured and Harvested Culture Supernatant. Determination of IL-12 in the Supernatant Detection these five lactobacilli: *Lactobacillus acidophilus* PM-A0002, *Lactobacillus gasseri* PM-A0005, *Lactobacillus salivarius* PM-A0006, *Lactobacillus johnsonii* PM-A0009, *Lactobacillus acidophilus* PM-A0013 which cocultured with dendritic cell can increase Th1 pathway cytokine, such as IL-12. This method can screen anti-allergy lactobacilli.

Figure 2:
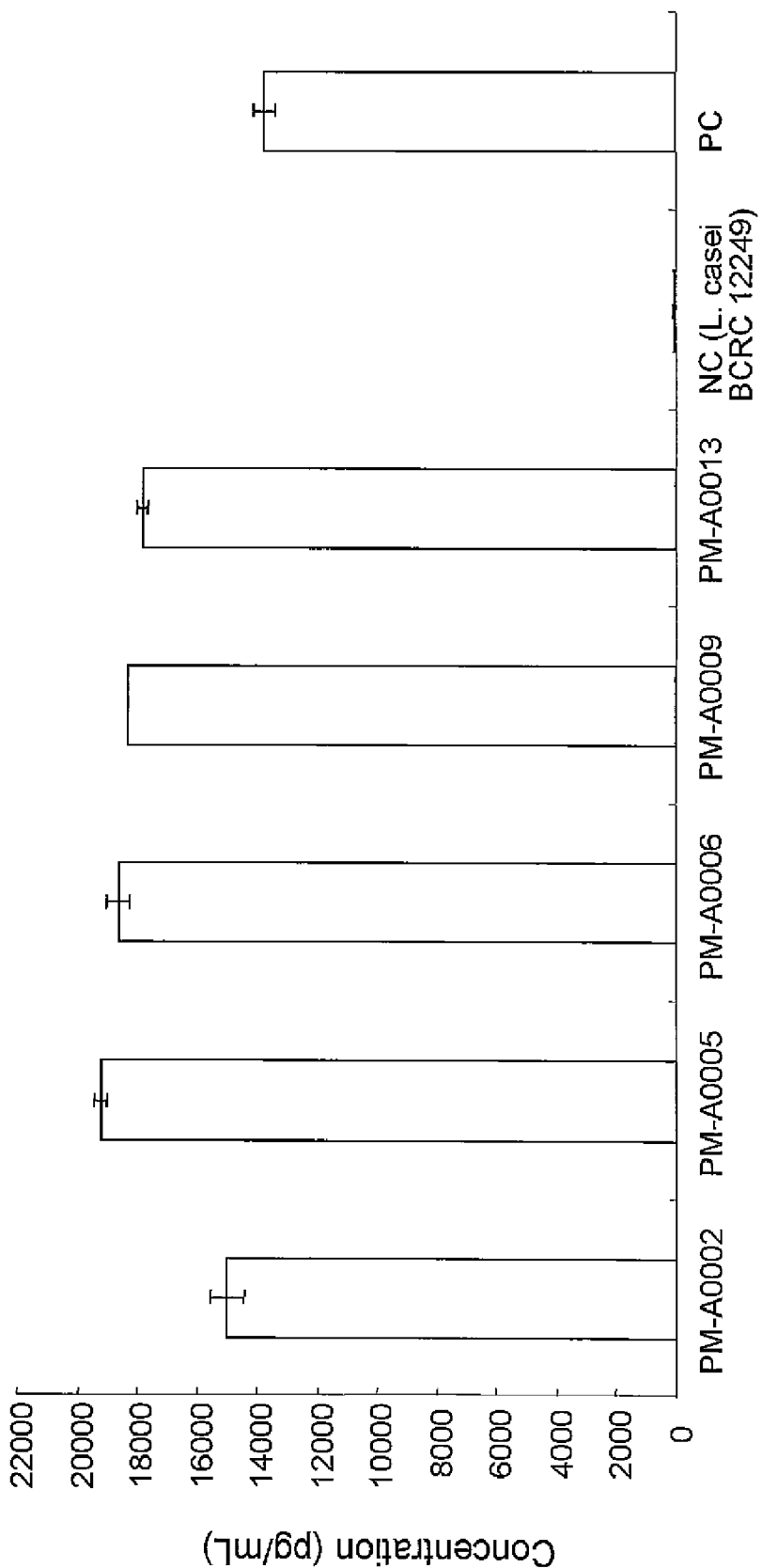
FIG. 2 shows the secretion of interleukin-12 (IL-12) in the co-culture of a heat-killed lactic acid bacterial strain and human dendritic cells (DC). The secretions of IL-12 were detected with ELISA after 48-hour co-culture of the heat-killed lactic acid bacterium and DCs, respectively. The amounts of IL-12 were expressed by the absorbance values (O.D. values). In the test, phytohemagglutinin (PHA) was used as positive control; *Lactobacillus casei* BCRC 12249 was used as negative control; bar 1 represents *Lactobacillus acidophilus* PM-A0002; bar 2 represents *Lactobacillus gasseri* PM-A0005; bar 3 represents *Lactobacillus salivarius* PM-A0006; bar 4 represents *Lactobacillus johnsonii* PM-A0009; bar 5 represents *Lactobacillus acidophilus* PM-A0013; bar 6 represents negative control; and bar 7 represents positive control.

The result is shown in table 4 and FIG. 2. The $10^5$~$10^7$ cells human dendritic cell were cultured with the heat-killed $10^6$~$10^8$ cfu lactobacilli: *Lactobacillus acidophilus* PM-A0002, *Lactobacillus gasseri* PM-A0005, *Lactobacillus salivarius* PM-A0006, *Lactobacillus johnsonii* PM-A0009, *Lactobacillus acidophilus* PM-A0013, and the contents of IL-12 in the culture supernatant were determined by ELISA. IL-12 was detected after 48 hours cocultured. The negative control is *Lactobacillus casei* BCRC 12249 which is no anti-allergy effect. The positive control is phytohemagglutinin (PHA). The result showed that human dendritic cell can increase IL-12 secretion by these five lactobacilli stimulating. There was significance of differences in the data.

TABLE 4

The secretion of IL-12 in the co-culture of a *Lactobacillus* strain and dendritic cells (Mean ± SD).

| Different *Lactobacillus* strain | IL-12 (pg/mL) |
| --- | --- |
| *Lactobacillus acidophilus* PM-A0002 | 15019 ± 569 |
| *Lactobacillus gasseri* PM-A0005 | 19222 ± 212 |
| *Lactobacillus salivarius* PM-A0006 | 18625 ± 365 |
| *Lactobacillus johnsonii* PM-A0009 | 18291 ± 39 |
| *Lactobacillus acidophilus* PM-A0013 | 17836 ± 168 |

TABLE 4-continued

The secretion of IL-12 in the co-culture of a *Lactobacillus* strain and dendritic cells (Mean ± SD).

| Different *Lactobacillus* strain | IL-12 (pg/mL) |
|---|---|
| Negative control (*L. casei* BCRC 12249) | 80 ± 15 |
| Positive control | 13786 ± 341 |

Example 4

Acid and Bile Tolerances of Five Lactobacilli Cells

Figure 3:
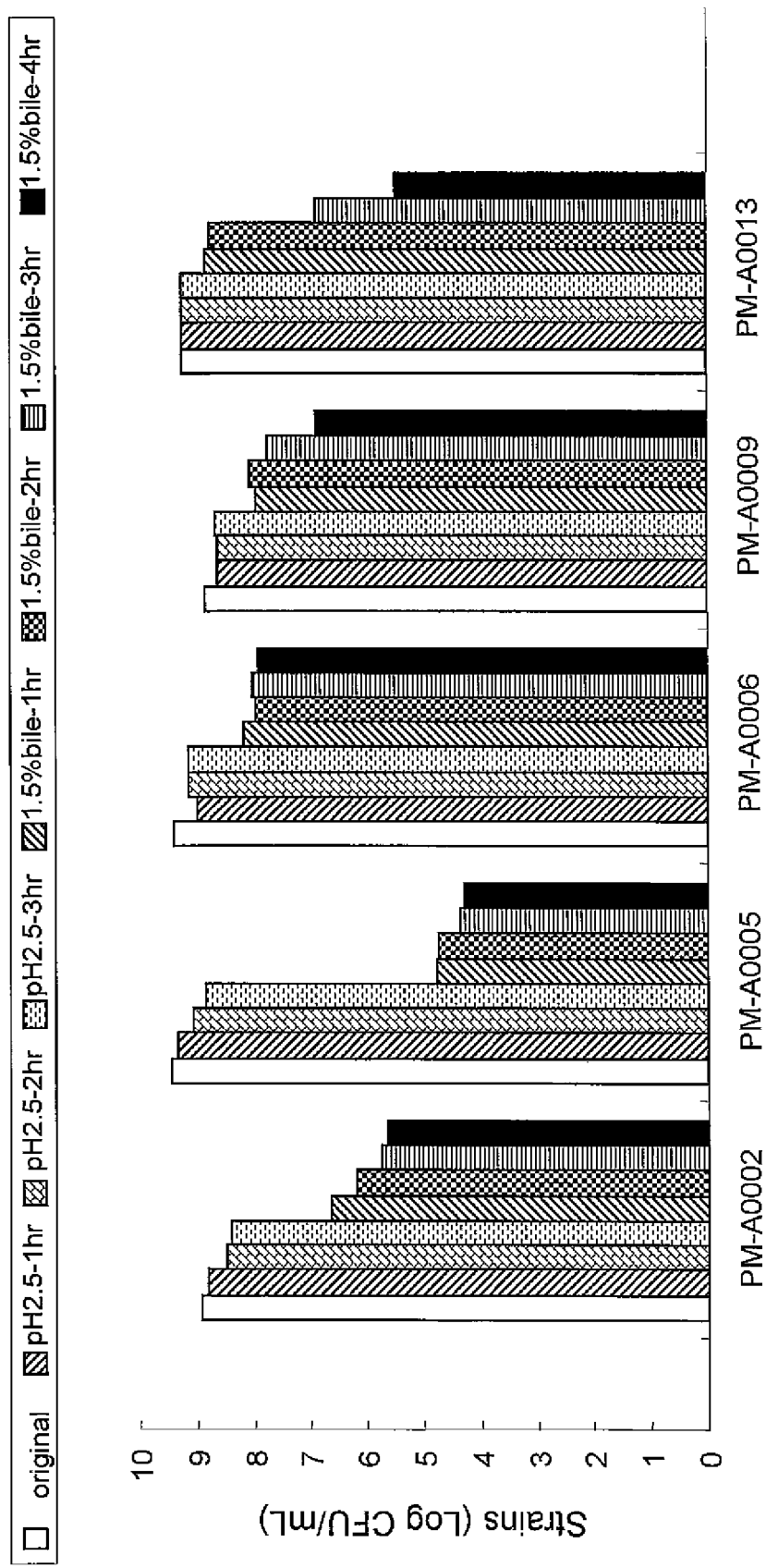
FIG. 3 shows the viability of lactobacillus cells in pH 2.5 MRS broth and 1.5% bile salt. All strains showed tolerance to pH 2.5 and 1.5% bile acid for 3 and 4 hours despite variations in the degree of viability. The patent deposit lactobacilli which had anti-allergy effect were the most acid-tolerance strains, with more than $10^8$ cfu/mL after incubation for 3 hours at pH 2.5. The *Lactobacillus acidophilus* PM-A0002, *Lactobacillus salivarius* PM-A0006, *Lactobacillus johnsonii* PM-A0009 and *Lactobacillus acidophilus* PM-A0013 were the most bile-tolerance strains, with more than $10^5$ cfu/mL after incubation for 4 hours at 1.5% bile MRS medium, the *Lactobacillus gasseri* PM-A0005 was the most bile-sensitive strains, with only $10^4$ total cfu/mL after the 4 hours incubation. Although the numbers of *Lactobacillus gasseri* PM-A0005 were decreased by 1.5% bile, it still had tolerance for bile acid. These results suggest that the five lactobacilli had tolerance for acid and bile acid in the human gastrointestinal tract.

The effect of acid on the viability of lactobacilli is shown in table 5 and FIG. 3. All strains showed tolerance to pH 2.5 for 3 hours despite variations in the degree of viability. The patent deposit lactobacilli which had anti-allergy effect were the most acid-tolerance strains, with more than $10^8$ cf/mL after incubation for 3 hours at pH 2.5.

The effect bile acid on the viability of lactobacilli is shown in table 6 and FIG. 3. All strains showed tolerance to 1.5% for 4 hours despite variations in the degree of viability. The *Lactobacillus acidophilus* PM-A0002, *Lactobacillus salivarius* PM-A0006, *Lactobacillus johnsonii* PM-A0009 and *Lactobacillus acidophilus* PM-A0013 were the most bile-tolerance strains, with more than $10^5$ cfu/mL after incubation for 4 hours at 1.5% bile MRS medium, the *Lactobacillus gasseri* PM-A0005 was the most bile-sensitive strains, with only $10^4$ total cfu/mL after the 4 hours incubation. Although the numbers of *Lactobacillus gasseri* PM-A0005 were decreased by 1.5% bile, it still had tolerance for bile acid. These results suggest that the five lactobacilli had tolerance for acid and bile acid in the human gastrointestinal tract.

TABLE 5

Viability of *lactobacillus* cells in pH 2.5 MRS broth.

| Different *Lactobacillus* strain | 0 h | pH 2.5-1 h | pH 2.5-2 h | pH 2.5-3 h |
|---|---|---|---|---|
| *Lactobacillus acidophilus* PM-A0002 | $8.20 \times 10^8$ | $6.50 \times 10^8$ | $2.87 \times 10^8$ | $2.51 \times 10^8$ |
| *Lactobacillus gasseri* PM-A0005 | $2.65 \times 10^9$ | $2.06 \times 10^9$ | $1.19 \times 10^9$ | $7.10 \times 10^8$ |
| *Lactobacillus salivarius* PM-A0006 | $2.55 \times 10^9$ | $9.70 \times 10^8$ | $1.42 \times 10^9$ | $1.43 \times 10^9$ |
| *Lactobacillus johnsonii* PM-A0009 | $6.87 \times 10^8$ | $4.05 \times 10^8$ | $4.15 \times 10^8$ | $4.35 \times 10^8$ |
| *Lactobacillus acidophilus* PM-A0013 | $1.78 \times 10^9$ | $1.83 \times 10^9$ | $1.86 \times 10^9$ | $1.73 \times 10^9$ |

TABLE 6

Viability of *lactobacillus* cells in 1.5% bile salt.

| Different *Lactobacillus* strain | 0 h | 1.5% bile - 1 h | 1.5% bile - 2 h | 1.5% bile - 3 h | 1.5% bile - 4 h |
|---|---|---|---|---|---|
| *Lactobacillus acidophilus* PM-A0002 | $8.20 \times 10^8$ | $4.30 \times 10^6$ | $1.50 \times 10^6$ | $5.45 \times 10^5$ | $4.40 \times 10^5$ |
| *Lactobacillus gasseri* PM-A0005 | $2.65 \times 10^9$ | $5.80 \times 10^4$ | $5.55 \times 10^4$ | $2.40 \times 10^4$ | $1.89 \times 10^4$ |
| *Lactobacillus salivarius* PM-A0006 | $2.55 \times 10^9$ | $1.45 \times 10^8$ | $9.20 \times 10^7$ | $1.02 \times 10^8$ | $8.30 \times 10^7$ |
| *Lactobacillus johnsonii* PM-A0009 | $6.87 \times 10^8$ | $8.65 \times 10^7$ | $1.13 \times 10^8$ | $5.70 \times 10^7$ | $8.30 \times 10^6$ |
| *Lactobacillus acidophilus* PM-A0013 | $1.78 \times 10^9$ | $6.72 \times 10^8$ | $5.73 \times 10^8$ | $8.00 \times 10^6$ | $3.00 \times 10^5$ |

Example 5

Adhesion Assay of *Lactobacillus* Cells with Caco-2 Cells

Figure 4:
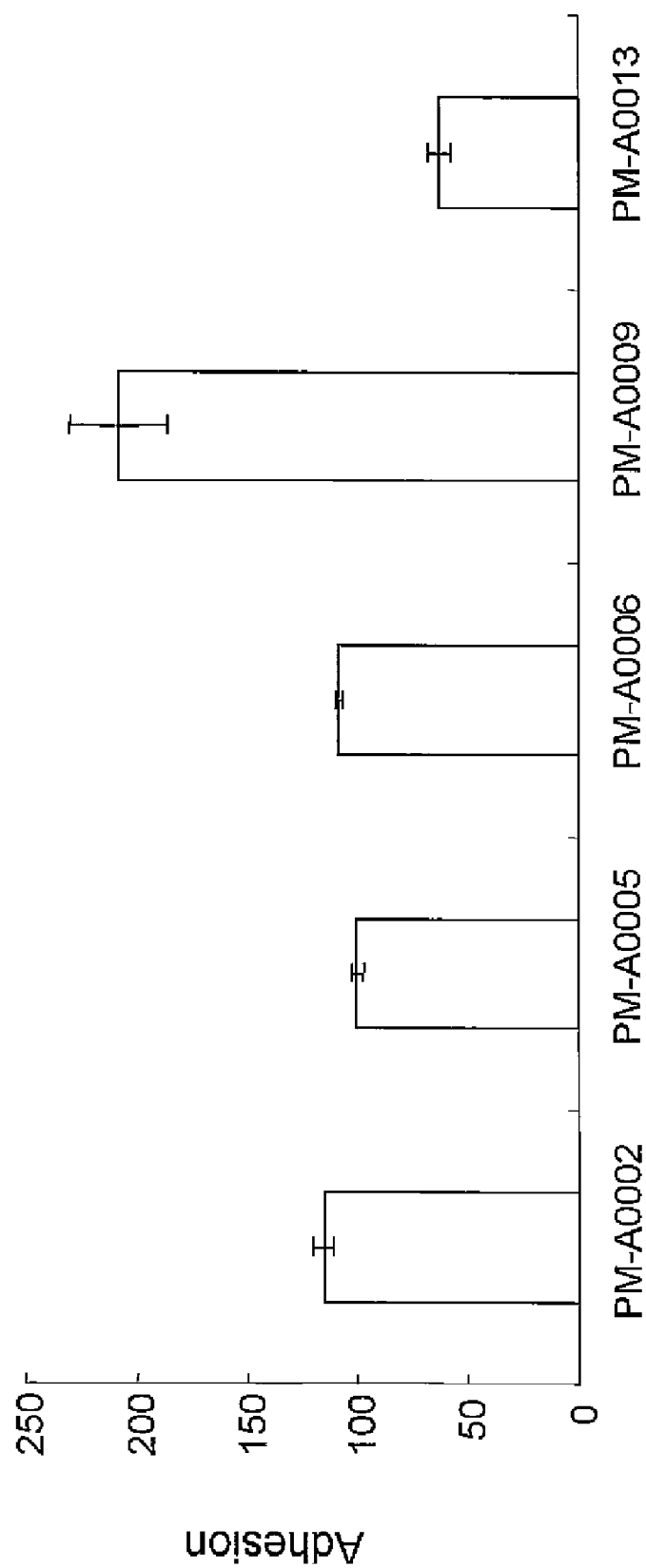
FIG. 4 shows the adhesion properties in gastrointestinal (GI) in the co-culture of a *Lactobacillus* strain and Caco-2 cell lines. The adhesion properties were detected with counting 15 random microscopic fields which were counted and average for each number. The amounts of adhesion properties in GI were expressed by counting lactobacillus cells number adhesion on Caco-2 cell lines. In the test, bar 1 represents *Lactobacillus acidophilus* PM-A0002; bar 2 represents *Lactobacillus gasseri* PM-A0005; bar 3 represents *Lactobacillus salivarius* PM-A0006; bar 4 represents *Lactobacillus johnsonii* PM-A0009; and bar 5 represents *Lactobacillus acidophilus* PM-A0013.

The adhesive results were shown in table 7 and FIG. 4. The adherent lactobacillus cells in 15 random microscopic fields were counted for each dish test. *Lactobacillus* strains were scored as nonadhesive when fewer then 40 *lactobacillus* cells were present in 45 fields, adhesive with 41 to 100 *lactobacillus* cells in 45 fields, and strongly adhesive with more than 100 lactobacillus cells in 45 fields. The *Lactobacillus* strains: *Lactobacillus acidophilus* PM-A0002, *Lactobacillus gasseri* PM-A0005, *Lactobacillus salivarius* PM-A0006, *Lactobacillus johnsonii* PM-A0009 were strongly adhesive, and *Lactobacillus acidophilus* PM-A0013 was adhesive, while the rest showed moderate-to-low adhesion.

TABLE 7

Adhesion properties of five *lactobacillus* cells (Mean ± SD).

| Different *Lactobacillus* strain | Means ± SD |
|---|---|
| *Lactobacillus acidophilus* PM-A0002 | 115.4 ± 4.4 |
| *Lactobacillus gasseri* PM-A0005 | 100.1 ± 2.6 |
| *Lactobacillus salivarius* PM-A0006 | 108.3 ± 1.4 |
| *Lactobacillus johnsonii* PM-A0009 | 208.3 ± 22.1 |
| *Lactobacillus acidophilus* PM-A0013 | 62.8 ± 5.0 |

Example 6

The In Vivo Platform in Animal Model for Anti-Allergy Lactic Acid Bacteria Screening Animals were intrapetitoneally sensitized with ovalbumin allergen and orally treated with *Lacrobacillus salivarius* PM-A0006 which had anti-allergy effect for 56 days. The moderated allergy evaluation was proceeded by the asthma animal model.

Region 1

Determination of ovalbumin-specific IgE.

Figure 6:
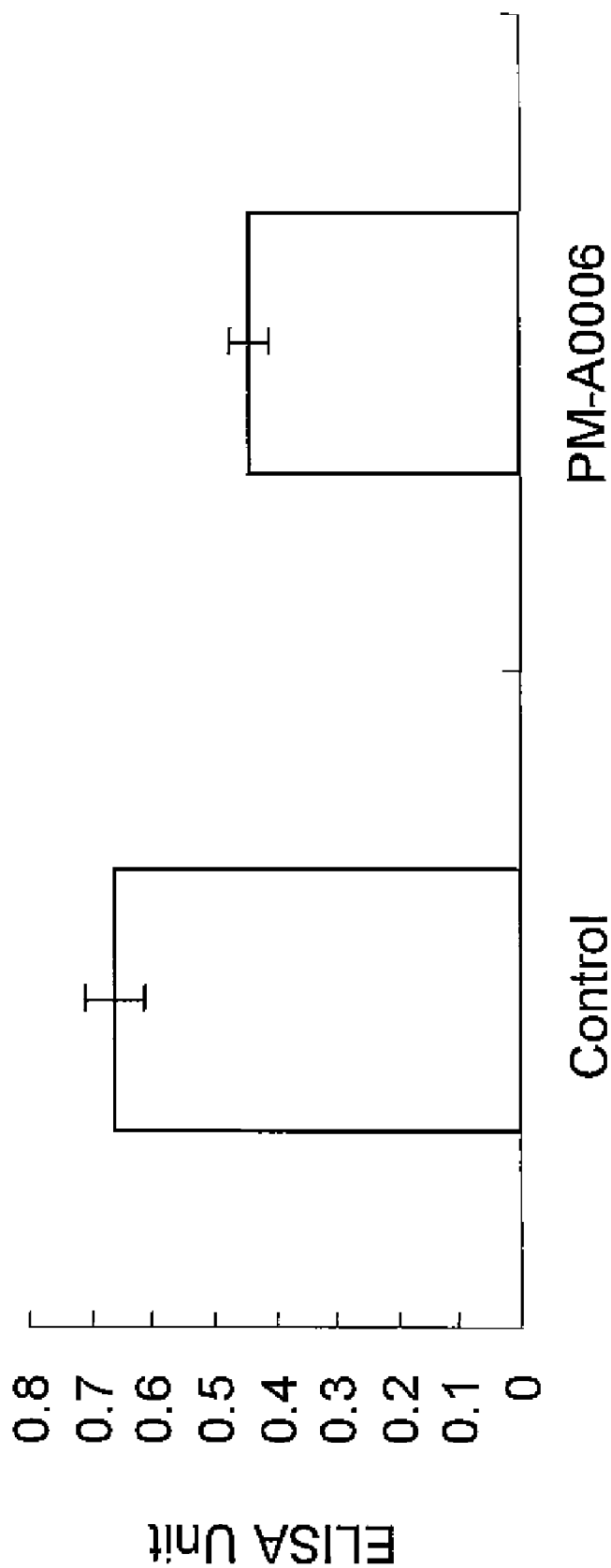
FIG. 6 shows detection of mice serum on ovalbumin-specific IgE production between oral uptakes of *lactobacillus* salivarius PM-A0006 oral uptake of placebo. Oral uptake of *lactobacillus salivarius* PM-A0006 can decrease ovalbumin-specific IgE in mouse serum.

The ovalbumin-specific IgE results were shown in table 8 and FIG. 6. Oral *Lactobacillus salivarius* PM-A0006 can decrease ovalbumin-specific IgE in mouse serum.

TABLE 8

Ovalbumain-specific IgE level in serum from ovalbumin-sensitized
BALB/c mice treated with *lactobacillus salivarius* PM-A0006 were
determined with ELISA. Values are expressed as mean ± SEM
(n = 14 per group).

| Group | Control | PM-A0006 |
| --- | --- | --- |
| IgE | 0.66 ± 0.05 | 0.44 ± 0.03 (P = 0.06)# |

ELISA unit = $(A_{sample} - A_{blank})/(A_{positive\ control} - A_{blank})$
P < 0.1

Region 2
Suppression of hyperreactivity (AHR) in vivo.
The AHR results were shown in table 9 and FIG. 7. The *Lactobacillus salivarius* PM-A0006 can suppress allergen-induced AHR which compared with control group (P<0.05).

TABLE 9

Airway responsiveness to aerosolized methacholine was measured in
unrestrained, conscious mice. Basal values were measured, followed by
measuring the response to nebulized saline and increasing concentrations
of methacholine (0, 6.25, 12.5, 25 and 50 mg/mL). Readings for breathing
parameters for a period of 3 min subsequent to each nebulization with
Penh were determined. Values are expressed as mean ± SEM
(n = 14 per group).

| Group (Mch: mg/mL) | Control (Penh) | PM-A0006 (Penh) |
| --- | --- | --- |
| 0 | 1.41 ± 0.05 | 1.44 ± 0.08 (P = 0.86) |
| 6.25 | 1.50 ± 0.11 | 1.35 ± 0.11 (P = 0.62) |
| 12.5 | 2.59 ± 0.24 | 1.94 ± 0.20 (P = 0.28) |
| 25 | 4.38 ± 0.47 | 1.95 ± 0.12 (P = 0.08)# |
| 50 | 5.10 ± 0.32 | 2.63 ± 0.13 (P = 0.002)* |

Mch = Methacholne
Penh = pause × PIF/PEF;
Pause = (Te − Tr)/Tr, (PIF: peak inspiratory flow; PEF: peak expiratory flow; Te: expiratory time; Tr: relaxation time)
*p < 0.05
P < 0.1

Region 3
Assessment of cells in bronchoalveolar lavage fluids (BALF).
The cell number of eosinophils in BALF results was shown in table 10 and FIG. 8. The number of cells in the BALF was used as a measure of the relative infiltration of cells into the airways. Significantly low numbers of eosinophils in the BALF of PM-A0006-treated mice were observed, when compared to control groups.

TABLE 10

The result was eosinophils cell percentage in the BALF. Values are
expressed as mean ± SEM. Per experimental group, 14 mice were used.

| Group | Control (%) | PM-A0006 (%) |
| --- | --- | --- |
| Eosinophil | 27.5 ± 1.37 | 17.1 ± 1.66 (P = 0.02)* |

% = In percentage %
*P < 0.05

Region 4
Assessment of supernatant in bronchoalveolar lavage fluids (BALF).
The cytokine and chemokine of supernatant in the BALF results were shown in table 11, FIG. 9 and FIG. 10. The cytokine and chemokine of supernatant in the BALE were detected by ELISA. Significantly low concentrations of eotaxin in the BALE of PM-A0006-treated mice were observed, when compared to control groups.

TABLE 11

The results were eotaxin and $PGE_2$ concentration in the BALF. Values are
expressed as mean ± SEM. Per experimental group, 14 mice were used.

| Group | Control | PM-A0006 |
| --- | --- | --- |
| Eotaxin (pg/mL) | 38.8 ± 3.00 | 22.7 ± 1.54 (P = 0.02)* |
| $PGE_2$ (ng/mL) | 8.1 ± 1.04 | 3.82 ± 0.41 (P = 0.08)# |

*P < 0.05
P < 0.1

Region 5
Augmentation of IFN-gamma production from splenocytes which were PM-A0006-treated mice by the addition of ConA in vitro.
The IFN-gamma production results were shown in table 12 and FIG. 11. ConA induced IFN-gamma production by splenocytes which was *Lactobacillus salivarius* PM-A0006-treated mice group higher than control mice group.

TABLE 12

ConA induced IFN-gamma production by splenocytes which were control
mice or PM-A0006-treated mice were cultured with constant concentration
(5 μg/mL) of ConA. After 48 h cultivation, the culture supernatant was
collected. The IFN-gamma levels were determined by ELISA, and the data
shown are the mean ± SEM.

| Group | Control | PM-A0006 |
| --- | --- | --- |
| ConA (pg/mL) | 5185 ± 558 | 9748 ± 966 (P = 0.05)* |

*P < 0.05

What is claimed is:
1. A biologically pure culture of a strain of lactic acid bacteria selected from the group consisting of:
   *Lactobacillus acidophilus* PM-A0002, CCTCC deposit number M 207038;
   *Lactobacillus gasseri* PM-A0005, CCTCC deposit number M 207039;
   *Lactobacillus salivarius* PM-A0006, CCTCC deposit number M 207040;
   *Lactobacillus johnsonii* PM-A0009, CCTCC deposit number M 207041; and
   *Lactobacillus acidophilus* PM-A0013, CCTCC deposit number M 207042.

* * * * *